United States Patent
Rouyer et al.

(10) Patent No.: US 9,243,228 B2
(45) Date of Patent: Jan. 26, 2016

(54) PROCESS FOR OBTAINING MYOFIBROBLASTS

(75) Inventors: Nicolas Jacques Rouyer, Roquefort les Pins (FR); Robert Barthel, Chateauneuf-Villevielle (FR)

(73) Assignee: Oncobiotek SA, Chateauneuf-Villevieille (FR)

( * ) Notice: Subject to any disclaimer, the term of this patent is extended or adjusted under 35 U.S.C. 154(b) by 0 days.

(21) Appl. No.: 13/386,522

(22) PCT Filed: Jul. 2, 2010

(86) PCT No.: PCT/EP2010/059478
§ 371 (c)(1),
(2), (4) Date: Apr. 4, 2012

(87) PCT Pub. No.: WO2011/009706
PCT Pub. Date: Jan. 27, 2011

(65) Prior Publication Data
US 2012/0190109 A1    Jul. 26, 2012

(30) Foreign Application Priority Data
Jul. 24, 2009 (FR) ..................... 09 55216

(51) Int. Cl.
C12N 5/071 (2010.01)
C12N 5/00 (2006.01)
C12N 5/02 (2006.01)
C12N 5/077 (2010.01)

(52) U.S. Cl.
CPC .......... *C12N 5/0656* (2013.01); *C12N 2500/25* (2013.01); *C12N 2500/90* (2013.01); *C12N 2501/11* (2013.01)

(58) Field of Classification Search
None
See application file for complete search history.

(56) References Cited

FOREIGN PATENT DOCUMENTS

EP    1715033    10/2006

OTHER PUBLICATIONS

Rando et al. "Primary mouse myoblast purification, characterization, and transplantation for cell-mediated gene therapy", Journal of Cell Biology 125(6): 1275-87, 1994.*
Imagawa et al. "Serum-free growth of normal and tumor mouse mammary epithelial cells in primary culture", PNAS 79: 4074-77, 1982.*
Ronnev-Jessen et al. "Identification, paracrine generation, and possible function of human breast carcinoma myofibroblasts in culture", In Vitro Cellular and Developmental Biology 28A: 273-283, 1992.*
Bernstein et al. "Urokinase receptor cleavage: a crucial step in fibroblast-to-myofibroblast differentiation", Molecular Biology of the Cell 18: 2716-27, 2007.*
Webber et al. "A human prostatic stromal myofibroblast cell line WPMY-1: a model for stromal-epithelial interaction in prostatic neoplasia", Carcinogenesis 20(7): 1185-92, 1999.*
Grupp et al. "A novel model to study renal myofibroblast formation in vitro", Kidney International 59: 543-553, 2001.*
Life Technologies™, DMEM-F12 product information, avaible online 2013.*
Masur et al. "Myofibroblasts differentiate from fibroblasts when plated at low density", PNAS 93: 4219-23, 1996.*
Allinen et al., "Molecular characterization of the tumor microenvironment in breast dancer", Cancer Cell. vol. 6, 2004, pp. 17-32.
Bernstein et al , "Urokinase receptor cleavage: a crucial step in fibroblast-to-myofibroblast differentiation", Molecular Biology of the Cell 18, 2007, pp. 2716-2727.
Bhowmick et al., "Stromal fibroblasts in cancer initiation and progression", Nature. Nov. 18, 2004. 432(7015), pp. 332-337.
Green, Michael R, "Senescence Not Just for Tumor Suppression", Cell, Aug. 2008, pp. 562-564.
Grupp, Clemens et al., "A novel model to study renal myofibroblast formation in vitro", Kidney International, vol. 59, No. 2, Feb. 2001, pp. 543-553.
Hammond et al., "Serum-free growth of human mammary epithelial cells: Rapid clonal growth in defined medium and extended serial passage with pituitary extract", PNAS, vol. 81, Apr. 12, 1984, pp. 5435-5439.
Hinz, Boris, "Formation and Function of the Myofibroblast during Tissue Repair", Journal of lnvestigstive Dermatology, Mar. 2007. vol. 127. No. 3, pp. 526-537.
Hinz, Boris, et al., "The Myofibroblast: One Function, Multiple Organs", The American Journal of Pathology, Jun. 2007, Vol, 170, No. 6, pp. 1807-1816.
Imagawa et al., "Serum-free growth of normal and tumor mouse mammary epithelial cells in primary culture", PNAS 79, 1982, pp. 4074-4077.

(Continued)

*Primary Examiner* — Taeyoon Kim
*Assistant Examiner* — Emily Cordas
(74) *Attorney, Agent, or Firm* — Honigman Miller Schwartz and Cohn LLP; Thomas A. Wootton; Jonathan P. O'Brien

(57) ABSTRACT

The invention relates to a process for obtention of myofibroblasts. According to this process:
  (a) a sample of cells essentially comprising fibroblasts is prepared; and
  (b) this sample of cells is cultured in a serum-free culture medium.

The main purpose addressed by the invention is to obtain a population of myofibroblasts, the characteristics whereof facilitate any study of these cells, and in particular as pure as possible a population of myofibroblasts.

Some examples of application of the invention are: identification of biomarkers of myofibroblasts, identification of therapeutic targets, identification and validation of anticancer compounds, and an in vitro model for the screening of pharmaceutical or cosmetic compounds.

8 Claims, 1 Drawing Sheet

(56) References Cited

OTHER PUBLICATIONS

International Search Report mailed Oct. 5, 2010 for PCT/EP2010/059478.
Iyer, VR et al, "The transcriptional program in the response of human fibroblasts to serum", Science, Jan. 1, 1999. 283(5398). pp. 83-87.
Jester, J. V. et al., "Induction of alpha-smooth muscle actin expression and myofibroblast transformation in cultured corneal keratocytes", Cornea, vol. 15, No. 5, Sep. 1996, pp. 505-516.
Kalluri, Raghu, "Fibroblasts in cancer", Nature Reviews Cancer 6, May 2006. pp. 392-401.
Khouw, Ilse M S. L. et al., "TBF-beta and bFGF affect the differentiation of proliferating porcine fibroblasts into myofibroblasts in vitro". Biomaterails, vol. 20, No. 10, Oct. 1999, pp. 1815-1822.
Kinnman et al., "Hepatic Stellate Cell Proliferation is an Early Platelet-Derived Growth Factor-Mediated Cellular Event in Rat Cholestatic Liver Injury", Lab Invest., vol. 81, No. 12, 2001, pp. 1700-1716.
Krizhanovsky et al., "Senescence of Activated Stellate Cells Limits Liver Fibrosis", Cell, vol. 134, issue 4, Aug. 22, 2006, pp. 657-667.
Life Technologies(TM). DMEM-F12 product information, avaiiable online 2013.
Marx, Jean, "All in the Stroma: Cancer's Cosa Nostra", Science, vol. 320, No. 5872, Apr. 4, 2008, pp. 38-41.
Micera, A et al., "Never growth factor (NGF) activates conjunctival myofibroblasts: a role for NGF in heaing processes and tissue remodeling", A.R.V.O. Annuai Meeting Abstract Search and Program Planner, 2002, and Annual Meeting of A.R.V.O., May 5-10, 2002.
Omary et al., "The pancreatic stellate cell: a star on the rise in pancreatic diseases", J. Clin. Invest., vol. 117, No. 1, Jan. 2007, pp. 50-59.
Orimo et al , "Stromal Fibroblasts Present in invasive Human Breast Carcinomas Promote Tumor Growth and Angiogenesis through Elevated SDF-1/CXCL 12 Secretion", Cell 2005, 121. pp. 335-348.
Orimo et al., Supplement to "Stromal Fibroblasts Present in Invasive Human Breast Carcinomas Promote Tumor Growth and Angiogenesis through Elevated SDF-1/CXCL12 Secretion", available at http://www.cell.com/supplemental/S0092-8674(05)00237-0.
Pan, Desi, "P311 induces a TGF-$\beta$1-independent, nonfibrogenic myofibroblast phenotype", J. Clin. Invest., Nov. 1, 2002, 110(9), pp. 1349-1358.
Rando et al., "Primary mouse myoblast purification, characterisation, and transplantation for cell-mediated gene therapy". Journal of Cell Biology 125 (6), 1994, pp. 1275-1287.
Ronnov-Jessen et al., "Identification, paracrine generation, and possible function of human breast carcinoma myofibroblasts in culture", In Vitro Cellular and Developmental Biology 28A, 1992, pp. 273-283.
Schafer et al., "Cancer as an overhealing wound: an old hypothesis revisited", Nature Reviews Molecular Cell Biology 9, Aug. 2008, pp. 626-638.
Stampfer et al., "Culture of Human Mammary Epithelial Cells", Published Online, Apr. 28, 2002, DOI: 10 1002/0471221201 ch4.
Webber, Mukta M. et al., "A human protstatic stromai myofibroblast cell line WPMY-1. A model for stromal-epithelial interactions in prostatic neoplasia", Carcinogenesis, vol. 20, No. 7, Jul. 1999, pp. 1185-1192.
Yamashita, M., et al., "Role of stromal myofibroblasts in invasive breast cancer; stromal expression of alpha-smooth muscle actin correlates with worse clinical outcome", Breast Cancer. Apr. 2012, vol. 19., No. 2, pp. 170-176.
Joyce, Johanna. "Therapeutic targeting of the tumor microenvironment", Cancer Cell, vol, 7, Jun. 2005, pp. 513-520.
Weinberg, Robert, "Coevolutton in the tumor microenvironment". Nature Genetics, vol. 40, No. 5, May 2008, pp. 494-495.

* cited by examiner

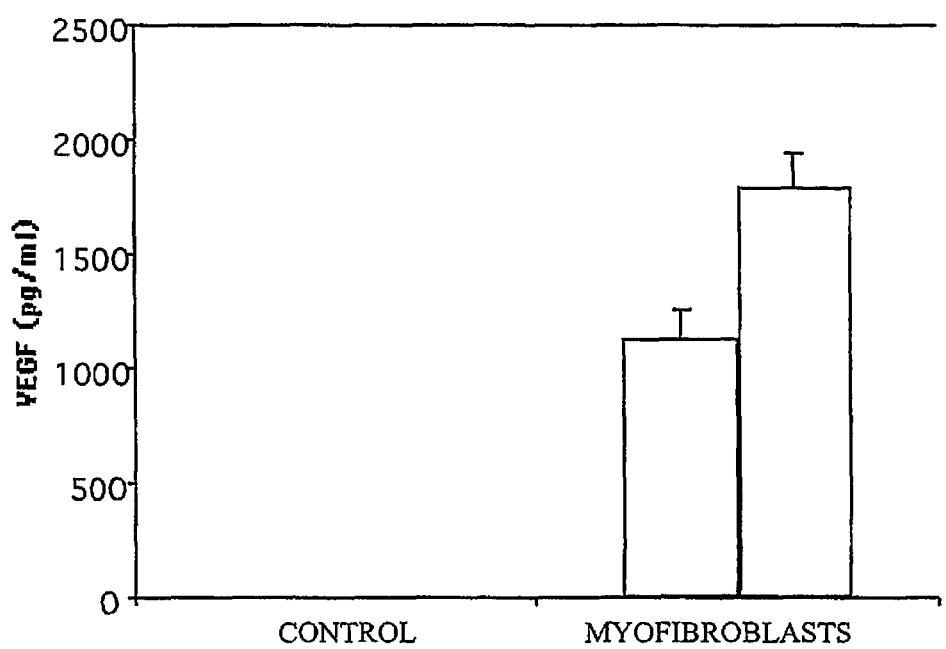

PROCESS FOR OBTAINING MYOFIBROBLASTS

This application is the U.S. National Phase of PCT Application Ser. No. PCT/EP2010/059478, filed Jul. 2, 2010, which claims the priority of French Application Ser. No. 0955216, filed Jul. 24, 2009, both of which are incorporated herein by reference in their entirety.

The present invention relates to a process for obtention of myofibroblasts.

In the description below, the references in square brackets ([ ]) refer to the list of references given at the end of the text.

The myofibroblasts represent a particular type of fibroblasts called CAFs, "carcinoma-associated fibroblasts", in other words fibroblasts associated with carcinoma. They are also involved in a variety of biological processes such as for example tissue remodeling.

They express the smooth muscle alpha-actin or SMA marker.

In what follows, the term fibroblast is used in the broad sense. It groups together not only the fibroblasts, here called fibroblasts "in the strict sense", but also the derivatives of fibroblasts such as activated fibroblasts, CAFs and myofibroblasts. Thus, the fibroblasts involved in tumoral processes are included, and also those involved in any other biological process in which myofibroblasts are involved.

In particular, the obtention of fibroblasts from a tumor by enzymatic digestion of the tumor, whether or not followed by one or more purification stages, is known (Orimo et al., Cell 2005, 121: 335-348 [1] or Allinen et al., Cancer Cell 2004, 6:17-32[2]).

Until now, cultures of fibroblasts have been made in a medium which contains serum, normally from 5 to 20% of serum, and contain a variable percentage of myofibroblasts.

For example, CAFs in a medium containing 5% of serum (Asterand), which are determined as such by simple visual inspection, are available commercially.

Academic laboratories produce populations of CAFs in culture medium containing 10% of serum. The phenotype of these cells is determined by measurement of the smooth muscle alpha-actin marker. Thus, these populations contain a variable percentage of CAFs, on average 30% at most.

Also available commercially are human hepatic myofibroblasts (Dominion Pharmakine) in a medium containing 20% of serum, only 50% to 60% of which express the smooth muscle alpha-actin (SMA) marker. In the liver and also in the pancreas, the cell from which the myofibroblast is derived is the stellate cell, which has the specific property of exhibiting spontaneous activation with expression of the SMA marker when it is cultured (Kinnman et al., Lab Invest 2001, 81:1709-1716[3]; Omary et al., JCI 2007, 117:50-59[4]).

The use of serum, for example fetal or newborn calf serum, nonetheless has the following disadvantages:
ethical problem connected with the collection of the serum,
the serum is a biological liquid the composition whereof is variable,
the exact composition of the serum is not known and it is not possible to precisely define the requirements of the cell,
serum contains factors (growth factors, antagonists, etc.) which can interfere with a test utilized in the pharmaceutical industry on cells in culture,
cells which are accustomed to grow in serum change phenotype or die when the serum is omitted from the culture medium.

To summarize, the populations of fibroblasts isolated from pathological tissues, as known and studied in vitro until now:
are heterogenous,
contain a variable percentage of myofibroblasts, and
grow in a medium which contains serum, the presence of which has the disadvantages mentioned above.

In this context, the main purpose addressed by the invention is to obtain a population of myofibroblasts, the characteristics whereof facilitate any study of these cells, and in particular as pure as possible a population of myofibroblasts.

For this purpose, the invention relates to a process for obtention of myofibroblasts, characterized in that:
(a) a sample of cells essentially comprising fibroblasts is prepared; and
(b) this sample of cells is cultured in a serum-free culture medium.

The sample of cells essentially comprising fibroblasts signifies that at least 50% of the cells which it contains are fibroblasts, preferably at least 70%. In any case, those skilled in the art will know how to evaluate, by routine experiments, the percentage of fibroblasts which the sample of cells must contain for the implementation of the invention.

The invention has the advantage of producing a population of myofibroblasts, purer than those of the prior art and which grow in a medium which does not contain serum.

Thus, the myofibroblasts obtained by the process according to the invention make it possible for example to study the biology of these cells precisely and reproducibly, and to identify potential therapeutic targets.

Owing to the absence of serum, they also make it possible to study the requirements of the cells and to define the factors which, for example, induce their differentiation, enable them to maintain their phenotype, sustain their multiplication and/or are involved in the premature senescence of these cells.

At the end of one or two passages in serum-free medium, the population of myofibroblasts obtained with the process according to the invention can amount to more than 95% of myofibroblasts.

The serum-free culture medium preferably comprises a serum-free basal medium which is a culture medium for epithelial cells. In fact, the culture medium obtained from such a basal medium makes it possible to obtain very good growth of the myofibroblasts.

This serum-free basal medium can in particular be a culture medium for human mammary epithelial cells. Alternatively, by way of example, this can be a serum-free culture medium known for the culturing of bronchial, placental or renal epithelial cells.

This serum-free basal medium can be supplemented by means of one or more supplements typically used in cell culture. As examples of supplements, hormones, growth factors, mitogens and antibiotics can be cited.

It can thus for example contain at least one supplement selected from insulin, hydrocortisone, epidermal growth factor or EGF, a bovine pituitary extract or BPE, and an antibiotic.

The antibiotic is not essential for good growth of the cells, but its presence prevents microbial contamination.

The antibiotic can for example be GA-1000 comprising gentamicin and amphotericin B, or normocin. Any antibiotic routinely used in cell culture can be used in the invention, and, by way of example, penicillin, streptomycin, ampicillin, kanamycin and tylosine can be cited.

For example, the serum-free culture medium according to the invention can be a culture medium for human mammary epithelial cells such as the medium commercially available under the name MEGM (Mammary Epithelial Growth Medium) (CAMBREX™). Currently Supplied by LONZA™

Alternatively, by way of example, this can be a serum-free culture medium known for the culturing of bronchial, placental or renal epithelial cells.

The starting formulation of MEGM is that of the medium MCDB 170 (Hammond et al., PNAS 1984, 81: 5435-5439 [5]). This medium MCDB 170, then MEGM, was developed and until now used specifically for the culturing of normal human mammary epithelial cells.

In the present invention, the use of this medium is particularly advantageous for the culturing of myofibroblasts.

It is made up of a basal medium, the exact formulation whereof is known under the name of MEBN medium (Mammary Epithelial Basal Medium) and five supplements: insulin, hydrocortisone, EGF, bovine pituitary extract and an antibiotic, GA-1000.

Ethanolamine and phosphoethanolamine are lipid precursors included in the basal formulation of MCDB 170 and in MEGM.

Another example of a serum-free basal medium which can be used in the invention is shown in table 1. The left-hand column lists the products contained in the composition of this medium. The right-hand column shows, for each product, its molar concentration in the medium, in moles per liter of medium.

This serum-free basal medium in fact comprises a mixture of the DMEM and HamF12 (INVITROGEN) culture media in 1:1 proportions.

This basal medium, mixed with EGF (PEPROTECH®), hydro-cortisone (SIGMA®), BPE (INVITROGEN), ITS-X (INVITROGEN) which includes insulin, transferrin and selenium, and an antibiotic such as normocin (INVIVOGEN), gives a serum-free culture medium which can be used in the invention. The culture medium obtained is called "serum-free DMEM/HamF12 culture medium".

The compositions of the DMEM and the HamF12 are those indicated for example in R. Ian Freshney, *"Culture of Animal Cells A Manual of Basic Technique"*, 2005[6].

TABLE 1

| Component | Molar concentration |
| --- | --- |
| L-alanine | $5 \times 10^{-5}$ |
| L-arginine | $7 \times 10^{-4}$ |
| L-asparagine | $5 \times 10^{-5}$ |
| L-aspartic acid | $5 \times 10^{-5}$ |
| L-cysteine | $10^{-4}$ |
| L-cystine | $10^{-4}$ |
| L-glutamic acid | $5 \times 10^{-5}$ |
| L-glutamine | $2.5 \times 10^{-3}$ |
| Glycine | $2.5 \times 10^{-4}$ |
| L-histidine | $1.5 \times 10^{-4}$ |
| L-isoleucine | $4.2 \times 10^{-4}$ |
| L-leucine | $4.5 \times 10^{-4}$ |
| L-lysine HCl | $5 \times 10^{-4}$ |
| L-methionine | $1.2 \times 10^{-4}$ |
| L-phenylalanine | $2.2 \times 10^{-4}$ |
| L-proline | $1.5 \times 10^{-4}$ |
| L-serine | $2.5 \times 10^{-4}$ |
| L-threonine | $4.5 \times 10^{-4}$ |
| L-tryptophan | $4.4 \times 10^{-5}$ |
| L-tyrosine | $2.1 \times 10^{-4}$ |
| L-valine | $4.5 \times 10^{-4}$ |
| Biotin | $1.5 \times 10^{-8}$ |
| Choline chloride | $6.4 \times 10^{-5}$ |
| Folic acid | $6 \times 10^{-6}$ |
| Myo-inositol | $7 \times 10^{-5}$ |
| Nicotinamide | $1.7 \times 10^{-5}$ |
| D-Ca pantothenate | $9.4 \times 10^{-6}$ |
| Pyridoxal HCl | $10^{-5}$ |
| Pyridoxine HCl | $1.5 \times 10^{-7}$ |
| Riboflavin | $5.8 \times 10^{-7}$ |

TABLE 1-continued

| Component | Molar concentration |
| --- | --- |
| Thiamine | $6.4 \times 10^{-6}$ |
| Vitamin B12 | $5 \times 10^{-7}$ |
| CaCl$_2$ | $1.1 \times 10^{-3}$ |
| KCl | $4.2 \times 10^{-3}$ |
| MgSO$_4$ | $4 \times 10^{-4}$ |
| NaCl | $1.2 \times 10^{-1}$ |
| NaHCO$_3$ | $2.9 \times 10^{-2}$ |
| NaH$_2$PO$_4$ | $4.5 \times 10^{-4}$ |
| Na$_2$HPO$_4$ | $5 \times 10^{-4}$ |
| CuSO$_4$ 5H$_2$O | $7.8 \times 10^{-9}$ |
| Fe(NO$_3$)$_3$ 9H$_2$O | $1.2 \times 10^{-7}$ |
| FeSO$_4$ 7H$_2$O | $1.5 \times 10^{-6}$ |
| ZnSO$_4$ 7H$_2$O | $1.5 \times 10^{-6}$ |
| Hypoxanthine | $1.5 \times 10^{-5}$ |
| Thymidine | $1.5 \times 10^{-6}$ |
| D-glucose | $1.8 \times 10^{-2}$ |
| Sodium pyruvate | $10^{-3}$ |
| Linoleic acid | $1.5 \times 10^{-7}$ |
| Lipoic acid | $5.1 \times 10^{-7}$ |
| Phenol red | $3.6 \times 10^{-5}$ |
| Putrescine | $5 \times 10^{-7}$ |

According to one embodiment of the invention, stage (a) comprises obtention of a cell suspension from a biological sample such as a biological tissue, then an initial culturing of the cells obtained in a culture medium favoring the growth of fibroblasts, for example in a culture medium containing serum.

According to another embodiment of the invention, stage (a) comprises obtention of a cell suspension from a biological sample such as a biological tissue, then a purification of cell subpopulations so as to obtain the sample of cells essentially comprising fibroblasts.

The obtention of a cell suspension from a biological sample can be effected by enzymatic digestion or by any other method such as mechanical dissociation or cell strainers.

Enzymatic digestion is preferred since this method is simple and effective.

The biological sample can be of any origin enabling it to comprise essentially fibroblasts.

Thus, it can come from any species of mammal.

In particular, the biological sample can be a tumor, preferably a carcinoma. Alternatively, it can be any other pathological tissue such as any tissue undergoing remodeling.

For the invention, the essential feature is that the biological sample contains fibroblasts and in particular myofibroblasts.

The percentage of myofibroblasts in the biological sample is evaluated on a histological section with immuno-histochemical labeling for smooth muscle alpha-actin.

By way of example, it is preferable to start from a biological sample at least 30%, or more preferably at least 50%, of the fibroblasts whereof have the myofibroblast phenotype.

Thus, the starting material for the culture can be any mammalian tissue which contains myofibroblasts, whether this be a tumor, for example a carcinoma, or a tissue being subjected to tissue remodeling or repair, such as in the case of fibrosis, cirrhosis, a scar or a wound. The myofibroblasts in fact play a key part in all these processes.

The culture medium favoring the growth of fibroblasts is more normally a medium containing serum. It can for example be a culture medium based on RPMI, DMEM or HAMF12.

To purify cell subpopulations in order to obtain the sample of cells essentially comprising fibroblasts, the protocol described by Allinen et al [2] or that described by Orimo et al [1] can for example be employed.

In the invention, it is possible to start from a complex mixture of epithelial and stromal cells, without prior purification. However, an initial culturing in a medium containing serum makes it possible to enrich the culture in fibroblast cells.

The invention also relates to a cell culture of myofibroblasts obtained by the process according to the invention, characterized in that at least 80%, or preferably at least 95%, of the cells which it contains are myofibroblasts.

This cell culture according to the invention is advantageously free of serum.

Such a cell culture makes it possible to study the effects of stimulation of the activity of the cells, such as for example in the case of wounds which do not heal, or of an angiogenesis deficit, or conversely the effects of an inhibition of the activity of the cells, such as in particular in the case of cancer, fibrosis, or cirrhosis.

The invention also relates to the use of the process according to the invention, to obtain a cell culture in which the cells comprise at least 80%, or preferably at least 95%, of myofibroblasts.

This cell culture is advantageously in a serum-free medium.

The invention further relates to the use of a serum-free culture medium, developed for the culturing of human mammary epithelial cells, for the obtention of myofibroblasts from a sample of cells essentially comprising fibroblasts.

This serum-free culture medium can contain at least one supplement selected for example from insulin, hydrocortisone, EGF, a bovine pituitary extract and an antibiotic.

In the invention, the cell culturing can be performed by the use of any appropriate means, in suspension or on a support, in a dish or in a flask, etc. Those skilled in the art are capable of selecting these means by drawing on their general knowledge.

Thus, some examples of application of the invention are: identification of biomarkers of myofibroblasts, identification of therapeutic targets, identification and validation of anticancer compounds, an in vitro model for the screening of pharmaceutical or cosmetic compounds, and in vitro toxicology.

Other characteristics and advantages of the invention will emerge clearly from the detailed description thereof which is given below, by way of indication, and in no way restrictively, with reference to FIG. 1, which represents a bar diagram of the quantity of VEGF produced by the myofibroblasts obtained according to the invention, in picograms per milliliter of medium.

Example of Process for Obtention of Myofibroblasts According to the Invention:

The starting point is a tumor taken from a mammal, in the present case a carcinoma taken from a dog.

By way of example, one modification would be to start from a cirrhotic liver to obtain a population of myofibroblasts involved in this pathological process.

A microscopic examination of the tumor can be performed to evaluate the percentage of myofibroblasts in the tumor, for example by means of immunohistochemical labeling of the tissue previously fixed in formalin.

Ideally, the starting point is a tumor which contains a high percentage of myofibroblasts, that is to say preferably at least 30% of the fibroblasts are myofibroblasts.

An enzymatic digestion of the tumor is performed, which may or may not be followed by a purification of cell subpopulations.

For the enzymatic digestion, which can be replaced by any other process making it possible to obtain a cell suspension, three different procedures can be followed:

1) the tissue is firstly kept at 4° C. during the microscopic examination of the tumor, while awaiting the results of that examination; a disadvantage is that the tissue is capable of degrading.

2) the enzymatic digestion of the tissue is performed, with or without purification of cell subpopulations, then the cells are frozen while awaiting the result of the microscopic examination.

3) the enzymatic digestion of the tissue is performed, and the culturing is started on the same day.

After the enzymatic digestion, it is possible not to perform a purification of cell subpopulations. In this case, the culturing is started in a medium to favor the growth of the fibroblasts. On the first passage, the cells are transferred into the serum-free MEGM medium.

Alternatively, after the enzymatic digestion, a purification of cell subpopulations can be performed. In this case, after that purification, the fraction containing the fibroblasts and derivatives is grown directly in the serum-free MEGM medium.

On each passage, immunocytochemistry can be used to determine the percentage of cells positive for the SMA marker.

The MEGM medium was developed specifically for the culturing of normal human mammary epithelial cells.

At the end of one or two passages, a culture of myofibroblasts which are more than 95% and up to 100% positive for the SMA marker is obtained.

The cells thus obtained have in particular the advantages of maintaining their phenotype in culture and of growing actively over about 4 passages. Only at the fifth passage do they show signs of cell death or senescence.

By following the same procedure as in the above example, with the sole difference that the MEGM culture medium is replaced by the serum-free DMEM/HamF12 culture medium described above, results similar to those obtained with the MEGM culture medium are obtained: at the end of one or two passages, a culture of myofibroblasts which are more than 95% and up to 100% positive for the SMA marker is obtained. However, with this serum-free DMEM/HamF12 culture medium, the cells grow less well from the fourth passage onwards.

Example of Experimental Protocol to be Followed for the Implementation of the Process for Obtention of Myofibroblasts According to the Invention:

The starting point is a mammary tumor, for example stored in a suitable transport medium.

The sample is rinsed in a saline phosphate buffer or PBS.

Pieces of tissue are transferred into a culture dish containing an enzyme cocktail: collagenase and hyaluronidase in a DMEM culture medium.

The tissue is torn into small fragments by means of two scalpels, and mixed thoroughly with a pipette.

The fragments obtained are placed in an incubator at 37° C. for a minimum of 2 hours.

DMEM is added to the tissue-enzyme cocktail mixture, and this is mixed thoroughly.

The tissue-enzyme cocktail-DMEM mixture is passed through a 40 micron nylon filter.

The mixture is centrifuged to give a cell pellet.

The cells obtained are washed with PBS, and again centrifuged.

The red corpuscles are removed, if necessary, with a red corpuscle lysis solution, and the cells are washed with PBS and again centrifuged to give a cell pellet.

The cells are taken up from the pellet into a small volume of PBS.

At this stage, the viability of the cells can be estimated, for example by staining with trypan blue, and the cells can be counted.

The culturing of these cells is then started in normal culture flasks, at $10^5$ cells per milliliter, in a medium which contains serum: RPMI culture medium +10% of heat-inactivated fetal calf serum (FBS);

On the following day, the culture medium is changed in order to remove the non-adherent cells.

A transfer into serum-free medium can be effected from the first passage, when the cells are at 80% confluence.

The antibiotic normally contained in the MEGM medium is GA-1000 which includes the antibiotics gentamicin and amphotericin-B. These antibiotics can in particular be replaced by normocin (Invivogen).

The serum-free medium is then replaced approximately every 3 to 4 days.

As mentioned above, the invention makes it possible to obtain a cell population comprising a high percentage (up to more than 95%) of myofibroblasts which grow in a medium which does not contain serum.

The cells thus obtained have in particular the advantages of maintaining their phenotype in culture and of growing actively over about 4 passages.

Further, these cells abundantly produce vascular endothelial growth factor or VEGF, VEGF being the principal pro-angiogenic molecule.

FIG. 1 illustrates the substantial production of VEGF by the myofibroblasts obtained with the invention.

It shows the concentration of canine VEGF in the supernatant of myofibroblasts at the fifth passage in the MEGM medium, on the first day (left-hand bar; right-hand part "MYOFIBROBLAST") and on the second day (right-hand bar; right-hand part "MYOFIBROBLAST"). The left-hand part of the FIGURE ("CONTROL") serves as the control; measurements were made in the culture medium alone.

The measurements were performed by means of a canine VEGF ELISA kit (R&D SYSTEMS®).

This FIGURE firstly confirms that the myofibroblasts are a substantial source of VEGF, the principal proangiogenic molecule. A tumor in fact needs to recruit blood vessels in order to establish itself and to grow beyond a certain size. It has been shown that cells of the stroma are diverted by the tumor for this purpose. In addition, the recruitment of new blood vessels is a key stage in tissue repair.

FIG. 1 further shows that the cells obtained by the invention can be used to screen pharmaceutical compounds with anti-angiogenic activity.

LIST OF REFERENCES

[1] Orimo et al., Cell 2005, 121: 335-348
[2] Allinen et al., Cancer Cell 2004, 6:17-32
[3] Kinnman et al., Lab Invest 2001, 81:1709-1716
[4] Omary et al., JCI 2007, 117:50-59
[5] Hammond et al., PNAS 1984, 81: 5435-5439
[6] R. Ian Freshney, "*Culture of Animal Cells A Manual of Basic Technique*", 2005

The invention claimed is:

1. A process for obtaining a serum-free liquid culture of cells wherein at least 80% of the cells in the cell culture are myofibroblast cells and wherein said myofibroblasts are obtained from the growth of myofibroblast cells wherein the biological sample is a carcinoma from mammalian tumor tissue, said process comprising:
   a) obtaining a cell sample from a carcinoma which contains both fibroblasts and myofibroblasts and where the percent of myofibroblasts in the sample is at least 30% of the total of both fibroblast and myofibroblast cells in the sample;
   b) transferring the cells from said sample into a culture medium that consists essentially of a serum-free culture medium suitable for growing mammary epithelial cells wherein said culture medium is selected from 1) MCDB170 or 2) a base of MCDB170 as a starting formulation and comprising insulin, hydrocortisone, epidermal growth factor (EGF), bovine pituitary extract, an antibiotic, ethanolamine and phosphoethanolamine;
   c) culturing the cells after transfer to the medium that consists essentially of a serum-free culture medium suitable for growing mammary epithelial cells wherein said culture medium is selected from 1) MCDB170 or 2) a base of MCDB170 as a starting formulation and comprising insulin, hydrocortisone, EGF, bovine pituitary extract, an antibiotic, ethanolamine and phosphoethanolamine for one or two passage;
   d) at the end of each passage the cells in the serum-free culture medium wherein said culture medium is selected from 1) MCDB170 or 2) a base of MCDB170 as a starting formulation and comprising insulin, hydrocortisone, EGF, bovine pituitary extract, an antibiotic, ethanolamine and phosphoethanolamine are evaluated using immunocytochemistry to determine the percentage of myofibroblasts which are positive for the alpha-smooth muscle actin (a-SMA) marker, in the cell culture medium;
   e) if after one or two passages the assay of the cells after passage in serum-free culture medium indicates at least 80% of the cells are myofibroblast cells, the process is complete, wherein said serum-free culture medium is selected from 1) MCDB170 or 2) a base of MCDB170 as a starting formulation and comprising insulin, hydrocortisone, EGF, bovine pituitary extract, an antibiotic, ethanolamine and phosphoethanolamine.

2. The process of claim 1, wherein said serum-free liquid culture medium is a base of MCDB170 as a starting formulation and comprises insulin, hydrocortisone, EGF, bovine pituitary extract, an antibiotic, ethanolamine and phosphoethanolamine.

3. The process of claim 1, wherein the cell sample in step a) is cultured in a culture medium favoring the growth of all fibroblasts, including myofibroblasts, wherein the culture medium contains serum.

4. The process of claim 2, wherein the cell sample in step a) is cultured in a culture medium favoring the growth of all fibroblasts, including myofibroblasts, wherein the culture medium contains serum.

5. The process of claim 1, wherein step a) comprises:
   an initial purification of said sample of cells, wherein said sample of cells are purified in order to obtain a sample of cells consisting essentially of fibroblasts.

6. The process of claim 2, wherein step a) comprises:
   an initial purification of said sample of cells, wherein said sample of cells are purified in order to obtain a sample of cells consisting essentially of fibroblasts.

7. The process of claim 5, wherein at least 50% of said fibroblasts in said initial cell culture of step a) are myofibroblasts.

8. The process of claim 6, wherein at least 50% of said fibroblasts in said initial cell culture of step a) are myofibroblasts.

* * * * *